United States Patent
Chang et al.

(10) Patent No.: US 11,988,625 B2
(45) Date of Patent: May 21, 2024

(54) CAPACITIVE BIOSENSOR AND FABRICATING METHOD THEREOF

(71) Applicant: Vanguard International Semiconductor Corporation, Hsinchu (TW)

(72) Inventors: Cheng-Ping Chang, Hualien (TW); Chien-Hui Li, Yilan (TW); Chien-Hsun Wu, Hsinchu (TW); Tai-I Yang, Hsinchu (TW); Yung-Hsiang Chen, Hsinchu (TW)

(73) Assignee: VANGUARD INTERNATIONAL SEMICONDUCTOR CORPORATION, Hsinchu (TW)

( * ) Notice: Subject to any disclaimer, the term of this patent is extended or adjusted under 35 U.S.C. 154(b) by 731 days.

(21) Appl. No.: 17/133,246

(22) Filed: Dec. 23, 2020

(65) Prior Publication Data

US 2022/0196586 A1    Jun. 23, 2022

(51) Int. Cl.
*G01N 27/22*  (2006.01)
*G01N 27/414* (2006.01)
*G01N 33/543* (2006.01)

(52) U.S. Cl.
CPC ....... *G01N 27/226* (2013.01); *G01N 27/4145* (2013.01); *G01N 33/5438* (2013.01)

(58) Field of Classification Search
None
See application file for complete search history.

(56) References Cited

U.S. PATENT DOCUMENTS

| 10,746,683 B2 * | 8/2020 | Cummins ......... G01R 27/2605 |
| 2005/0045867 A1 * | 3/2005 | Ozkan .................. H01L 29/22 438/105 |

(Continued)

FOREIGN PATENT DOCUMENTS

| CN | 101558295 A | * 10/2009 | ......... G01N 33/5438 |
| CN | 102005464 A |   4/2011 | |

(Continued)

OTHER PUBLICATIONS

Taiwanese Office Action and Search Report for Taiwanese Application No. 109132846, dated Jun. 17, 2021.

(Continued)

*Primary Examiner* — Michael Lebentritt
(74) *Attorney, Agent, or Firm* — Birch, Stewart, Kolasch & Birch, LLP

(57) ABSTRACT

A capacitive biosensor is provided. The capacitive biosensor includes: a transistor, an interconnect structure on the transistor, and a passivation layer on the interconnect structure. The interconnect structure includes a first metal structure on the transistor, a second metal structure on the first metal structure, and a third metal structure on the second metal structure. The third metal structure includes a first conductive layer, a second conductive layer, and a third conductive layer that are sequentially stacked. The passivation has an opening exposing a portion of the third metal structure. The capacitive biosensor further includes a sensing region on the interconnect structure. The sensing region includes a first sensing electrode and a second sensing electrode. The first sensing electrode is formed of the third conductive layer, and the second sensing electrode is disposed on the passivation layer.

20 Claims, 8 Drawing Sheets

(56) References Cited

U.S. PATENT DOCUMENTS

| | | |
|---|---|---|
| 2010/0122904 A1 | 5/2010 | Hassibi et al. |
| 2010/0248284 A1 | 9/2010 | Chen et al. |
| 2013/0186754 A1* | 7/2013 | Ackerson ............... H01L 24/03 |
| | | 438/653 |
| 2013/0345065 A1 | 12/2013 | Hassibi et al. |
| 2017/0184541 A1 | 6/2017 | Lin et al. |
| 2019/0366102 A1* | 12/2019 | Holmes ............. A61N 1/36071 |

FOREIGN PATENT DOCUMENTS

| | | | |
|---|---|---|---|
| JP | 2012-47536 A | 3/2012 | |
| TW | 594922 B | 6/2004 | |
| TW | 201803020 A | 1/2018 | |
| WO | WO-2012042399 A1 * | 4/2012 | ......... G01N 27/4145 |

OTHER PUBLICATIONS

Taiwanese Office Action and Search Report for Taiwanese Application No. 109132846, dated Aug. 17, 2021.

* cited by examiner

CAPACITIVE BIOSENSOR AND FABRICATING METHOD THEREOF

BACKGROUND

Technical Field

The present disclosure relates to a biosensor and a fabricating method thereof, and in particular, it relates to a capacitive biosensor and a fabricating method thereof.

Description of the Related Art

Biosensors are devices used for sensing and detecting biomolecules. They operate on the basis of electronic, electrochemical, optical, and mechanical detection principles. Biosensors that include transistors are sensors that electrically sense charges, photons, and the mechanical properties of biomolecules. This detection may be performed by detecting the biomolecules themselves, or through interactions and reactions between specified reactants and biomolecules. Such biosensors may be fabricated using semiconductor processes, and they may quickly convert electric signals. Such biosensors may find application in integrated circuits (ICs) and microelectromechanical systems (MEMS).

SUMMARY

In accordance with some embodiments of the disclosure, a capacitive biosensor is provided. The capacitive biosensor includes: a transistor; an interconnect structure disposed on the transistor; a passivation layer disposed on the interconnect structure; and a sensing region disposed on the interconnect structure. The interconnect structure includes: a first metal structure disposed on the transistor; a second metal structure disposed on the first metal structure; and a third metal structure disposed on the second metal structure. The third metal structure includes a first conductive layer, a second conductive layer, and a third conductive layer that are sequentially stacked. Each of the first conductive layer and the third conductive layer includes a first conductive coating and a second conductive coating on the first conductive coating. The passivation layer has an opening exposing a portion of the third metal structure. The sensing region includes a first sensing electrode and a second sensing electrode. The first sensing electrode is formed of the third conductive layer, and the second sensing electrode is disposed on the passivation layer.

In accordance with some embodiments of the disclosure, a method for fabricating a capacitive biosensor is provided. The method includes providing a transistor and forming an interconnect structure on the transistor. The interconnect structure includes: a first metal structure disposed on the transistor; a second metal structure disposed on the first metal structure; and a third metal structure disposed on the second metal structure. The third metal structure includes a first conductive layer, a second conductive layer, and a third conductive layer that are sequentially stacked. The third conductive layer forms a first sensing electrode of a sensing capacitor. The method further includes: depositing a passivation layer on the interconnect structure; depositing a second sensing electrode of the sensing capacitor on a portion of the passivation layer; and forming an opening in the passivation layer exposing a portion of the third metal structure.

BRIEF DESCRIPTION OF THE DRAWINGS

Aspects of this disclosure are best understood from the following detailed description when read with the accompanying figures. It should be noted that, in accordance with common practice in the industry, various features are not drawn to scale. In fact, the dimensions of the various features may be arbitrarily increased or reduced for clarity of discussion.

DETAILED DESCRIPTION

Figure 1:
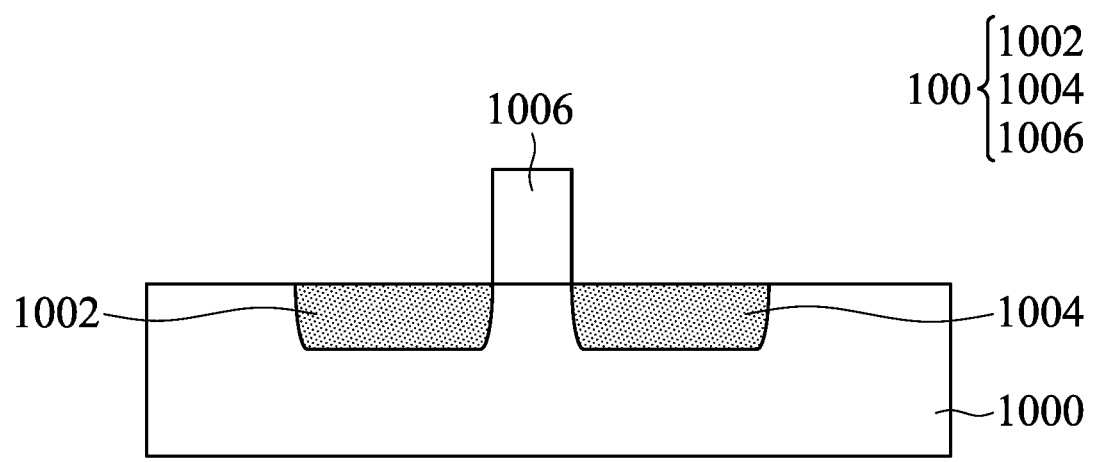
FIGS. 1-4, and 5A are cross-sectional diagrams of intermediate stages of a process for fabricating a capacitive biosensor in accordance with some embodiments of the disclosure.

The following disclosure provides many different embodiments, or examples, for implementing different features of the subject matter provided. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features. In addition, the present disclosure may repeat reference numerals and/or letters in the various examples. This repetition is for the purpose of simplicity and clarity and does not in itself dictate a relationship between the various embodiments and/or configurations discussed.

Furthermore, spatially relative terms, such as "beneath", "below", "lower", "over", "above", "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

The terms "about", "approximately" and "substantially" typically mean+/−20% of the stated value, more typically+/−10% of the stated value and even more typically+/−5% of the stated value, more typically+/−3% of the stated value, more typically+/−2% of the stated value, more typically+/−1% of the stated value and even more typically+/−0.5% of the stated value. It should be noted that the stated value of the disclosure is an approximate value. When there is no specific description, the stated value includes the meaning of "about", "approximately" or "substantially".

Although some embodiments are discussed with operations performed in a particular order, these operations may be performed in another logical order. Additional features can be provided to the semiconductor structures in embodiments of the present disclosure. Some of the features described below can be replaced or eliminated for different embodiments.

The embodiments of the present disclosure provide a capacitive biosensor that may be compatible with the existing MOS processes. In the back end of line (BEOL) process of MOS, the conductive coating of the topmost metal structure in the interconnect structure may be directly used as a first sensing electrode of the capacitive biosensor without deposition additional layer for the first sensing electrode. Since the resistance of the existing material of the first and second sensing electrodes is high, larger conductive pillars are required to reduce resistance, thereby leading to higher manufacturing cost. In contrast, the complexity and cost of the process for the capacitive biosensor may be reduced according to the embodiments of the disclosure. In addition, the embodiments of the disclosure make use of sidewall spacers to protect the first and second sensing electrodes of the capacitive biosensor so that the first and second sensing electrodes may not be etched by acid components in bio-samples. Damage to the sensing electrodes of the capacitive biosensor may affect attachment of bio-samples, and the capacitance measured may be affected accordingly, thus resulting in lower sensitivity of the capacitive biosensor.

FIGS. 1-4, and 5A are cross-sectional diagrams of intermediate stages of a process for fabricating a capacitive biosensor 10 in accordance with some embodiments of the disclosure. In particular, FIG. 1 is a simplified diagram of the capacitive biosensor 10 according to some embodiments of the disclosure. In FIG. 1, a transistor 100 is disposed on a substrate 1000, and includes a source region 1002, a drain region 1004, and a gate 1006. The source region 1002 and the drain region 1004 are formed in the substrate 1000, and the gate 1006 is formed on the substrate 1000. The transistor 100 as shown in FIG. 1 is merely exemplary, and the invention is not limited thereto. The transistor 100 may be any types of transistors, such as a PMOS field-effect transistor (PMOSFET), a NMOSFET, or a complementary MOSFET (CMOSFET).

Figure 2:
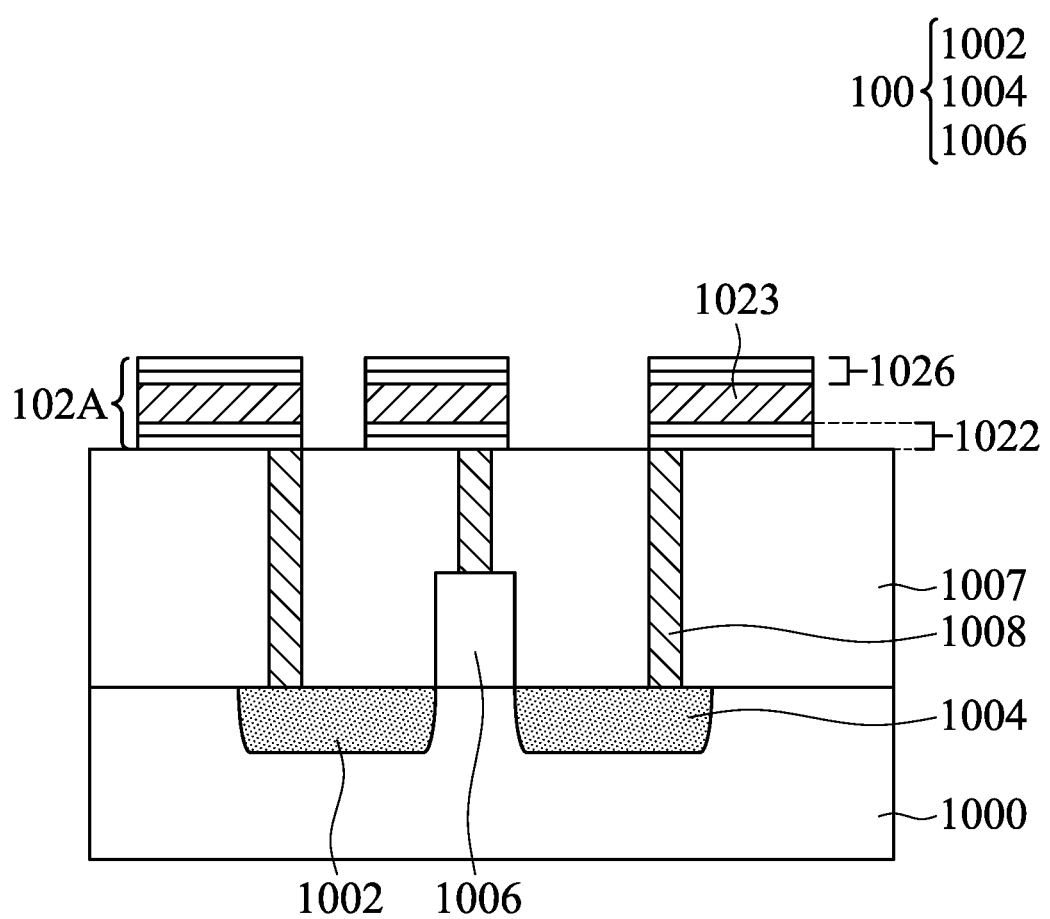

Referring to FIG. 2, a dielectric layer 1007 and contacts 1008 are further formed on the transistor 100. The dielectric layer 1007 is formed on the substrate 1000. The dielectric layer 1007 may include a multi-layered structure formed of one or more dielectric materials, such as silicon oxide, silicon nitride, silicon oxynitride, phosphosilicate glass (PSG), borophosphosilicate glass (BPSG), a low-k dielectric material, other suitable dielectric materials, or a combination thereof. The low-k dielectric material may include fluorinated silicate glass (FSG), carbon doped silicon oxide, amorphous fluorinated carbon, parylene, benzocyclobutenes (BCB), polyimide (PI), or a combination thereof.

The contacts 1008 are formed penetrating through the dielectric layer 1007, and respectively contact the source region 1002, the drain region 1004, and the gate 1006 to form an electrical connection between the transistor 100 and an interconnect structure that is subsequently formed. The contacts 1008 may include any suitable conductive materials, such as Al, Cu, W, Ti, Ta, TiN, TaN, NiSi, CoSi, TaC, TaSiN, TaCN, TiAl, TiAlN, other suitable conductive materials, or a combination thereof.

Still referring to FIG. 2, a metal layer 1023 of a first metal structure 102A in an interconnect structure 102 is formed on the transistor 100. For example, the material of the metal layer 1023 are deposited on the transistor 100 first, and then a portion of the material of the metal layer 1023 may be removed using suitable etching processes to form the first metal structure 102A. The metal layer 1023 may include any suitable materials, such as Al, Cu, W, Ti, Ta, TiN, TaN, NiSi, CoSi, TaC, TaSiN, TaCN, TiAl, TiAlN, other suitable conductive materials, or a combination thereof. The material of the metal layer 1023 may be deposited by physical vapor deposition (PVD), atomic layer deposition (ALD), metal-organic chemical vapor deposition (MOCVD), other suitable deposition techniques, or a combination thereof.

In some embodiments, as shown in FIG. 2, the first metal structure 102A may further include other layers disposed above or below the metal layer 1023 (e.g., layers 1022 and 1026). The other layers will be described in detail below. In some embodiments, the material of the metal layer 1023 may be deposited first, and then a portion of the material of the metal layer 1023 may be removed using suitable etching processes to form the first metal structure 102A.

Figure 3:
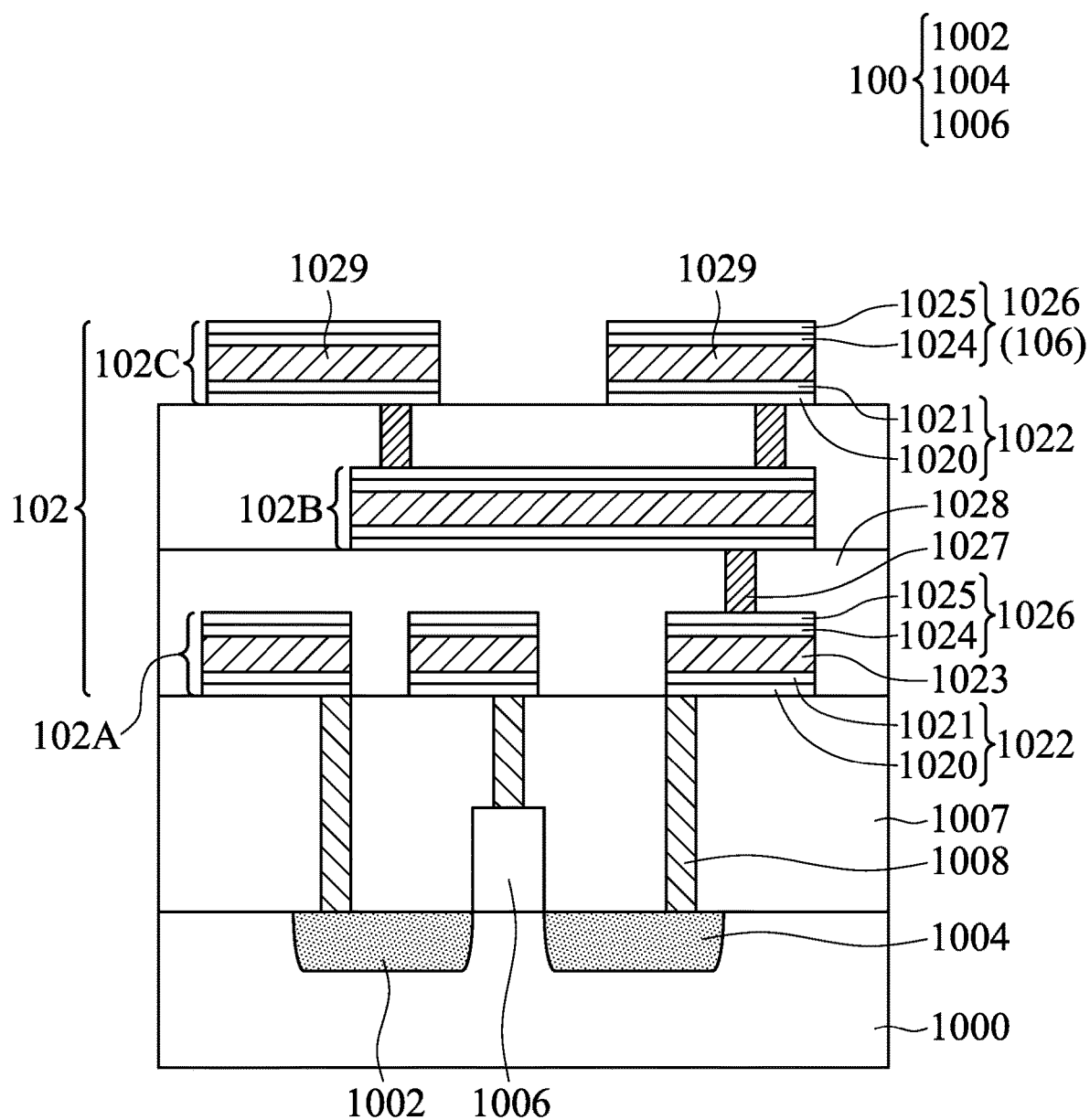

Next, referring to FIG. 3, an inter-metal dielectric (IMD) layer 1028 is formed on the dielectric layer 1007. The material of the inter-metal dielectric layer 1028 may be similar to or the same as the material of the dielectric layer 1007, which is not repeated herein. In some other embodiments, in addition to the aforementioned method for forming the first metal structure 102A, a damascene process may be also used for the formation of the first metal structure 102A in the inter-metal dielectric layer 1028. Specifically, the inter-metal dielectric layer 1028 is deposited first, and then trench openings for accommodating the first metal structure 102A are formed in the inter-metal dielectric layer 1028. Subsequently, the materials of a first conductive layer 1022, the metal layer 1023, and a third conductive layer 1026 are respectively deposited on the inter-metal dielectric layer 1028 and are filled in the openings. A planarization process is performed to remove excess materials to form the first metal structure 102A.

After forming the inter-metal dielectric layer 1028, several openings (not shown) are formed in the inter-metal dielectric layer 1028 by a patterning process, and the metal materials are deposited on the inter-metal dielectric layer 1028 by suitable deposition processes to fill the openings and form conductive pillars 1027. The material for the conductive pillars 1027 may be similar to or the same as the material of the contacts 1008, which is not repeated herein. The patterning process may include a photolithography process and an etching process. In some embodiments, the photolithography process may include photoresist coating, soft baking, hard baking, mask aligning, exposure, post-exposure baking, developing the photoresist, rinsing, drying, or other suitable processes. In some embodiments, the etching process may include a dry etching process, a wet etching process, or a combination thereof. For example, the dry etching process may include a reactive ion etching (RIE) process or a plasma etching process. Next, more metal structures (a second metal structure 102B and a third metal structure 102C as shown in FIG. 3) may be formed using the same deposition process and patterning process as described above.

As shown in FIG. 3, the interconnect structure 102 is a multi-layered structure formed of the first metal structure 102A, the second metal structure 102B, the third metal structure 102C, the inter-metal dielectric layer 1028, and the conductive pillars 1027. However, it should be noted that the number of the metal structures and the conductive pillars in the interconnect structure 102 as shown in FIG. 3 and the following figures are merely exemplary, and the invention is not limited thereto. That is, the interconnect structure 102 of the embodiments of the disclosure may include more metal structures and conductive pillars. For example, the third metal structure 102C (of which the projected area is identical to the projected area of a first sensing electrode 106 of the capacitive biosensor 10) may be electrically connected to the second metal structure 102B through at least two conductive pillars 1027. The metal layer of the third metal structure 102C in the interconnect structure 102 is herein referred to as a topmost metal layer 1029.

As shown in FIG. 3, the third metal structure 102C further includes the first conductive layer 1022 and the third conductive layer 1026, and the topmost metal layer 1029 is used as a second conductive layer of the third metal structure 102C. That is, the third metal structure 102C includes the first conductive layer 1022, the second conductive layer 1029, and the third conductive layer 1026.

In particular, prior to the formation of the second conductive layer 1029, the first conductive layer 1022 may be formed on the interconnect structure 102 first to enhance adhesion of the metal layer 1023 to the interconnect structure 102. In some embodiments, the first conductive layer 1022 may include a first conductive coating 1020 and a second conductive coating 1021 disposed on the first conductive coating 1020. The material of the first conductive coating 1020 may include titanium, tantalum, ruthenium, and the like, or a combination thereof. In one specific embodiment, the material of the first conductive coating 1020 may be titanium. The material of the second conductive coating 1021 may include titanium nitride, titanium oxide, tantalum nitride, tantalum oxide, ruthenium nitride, ruthenium oxide, and the like, or a combination thereof. In one specific embodiment, the material of the second conductive coating 1021 may be titanium nitride. The first conductive coating 1020 and the second conductive coating 1021 may be deposited using suitable deposition processes, such as physical vapor deposition, atomic layer deposition, metal-organic chemical vapor deposition, other suitable deposition techniques, or a combination thereof. In some embodiments, the thickness of the first conductive coating 1020 may range from about 100 Å to about 300 Å, such as about 200 Å. In some embodiments, the thickness of the second conductive coating 1021 may range from about 1000 Å to about 2000 Å, such as about 1500 Å.

Furthermore, the third conductive layer 1026 is formed on the second conductive layer 1029. The third conductive layer 1026 of the third metal structure 102C will be used as the first sensing electrode of the capacitive biosensor 10, which is also designated as the reference number 106. In some embodiments, the third conductive layer 1026 may include a first conductive coating 1024 and a second conductive coating 1025 disposed on the first conductive coating 1024. The material of the first conductive coating 1024 may include titanium, tantalum, ruthenium, and the like, or a combination thereof. In one specific embodiment, the material of the first conductive coating 1024 may be titanium. The material of the second conductive coating 1025 may include titanium nitride, titanium oxide, tantalum nitride, tantalum oxide, ruthenium nitride, ruthenium oxide, and the like, or a combination thereof. In one specific embodiment, the material of the second conductive coating 1025 may be titanium nitride. The first conductive coating 1024 and the second conductive coating 1025 may be deposited using suitable deposition processes, such as physical vapor deposition, atomic layer deposition, metal-organic chemical vapor deposition, other suitable deposition techniques, or a combination thereof. In some embodiments, the thickness of the first conductive coating 1024 may range from about 100 Å to about 300 Å, such as about 200 Å. In some embodiments, the thickness of the second conductive coating 1025 may range from about 1000 Å to about 2000 Å, such as about 1500 Å.

As described above, in some embodiments, the first metal structure 102A and the second metal structure 102B may further include the first conductive layer 1022 and the second conductive layer 1026. In these embodiments, the first conductive layer 1022 may include the first conductive coating 1020 and the second conductive coating 1021, and the third conductive layer 1026 may include the first conductive coating 1024 and the second conductive coating 1025.

It should be noted that although the first metal structure 102A and the second metal structure 102B of the interconnect structure 102 are illustrated to have the same number of layers in FIGS. 2, 3, and the following figures, the invention is not limited thereto. In other embodiments, the first metal structure 102A and the second metal structure 102B may also include 2 to 6 conductive layers being the same or different. In some embodiments, the first metal structure 102A and the second metal structure 102B may not include other layers in addition to the metal layer 1023.

By using the third conductive layer 1026 of the third metal structure 102C in the interconnect structure 102 as the first sensing electrode 106, the subsequent processes may be compatible with the existing MOS BEOL process. Additional processes for the formation of a layer for the first sensing electrode is not required. In this way, the complexity and cost of the process may be reduced, and the thickness of the entire device may be also reduced.

Figure 4:
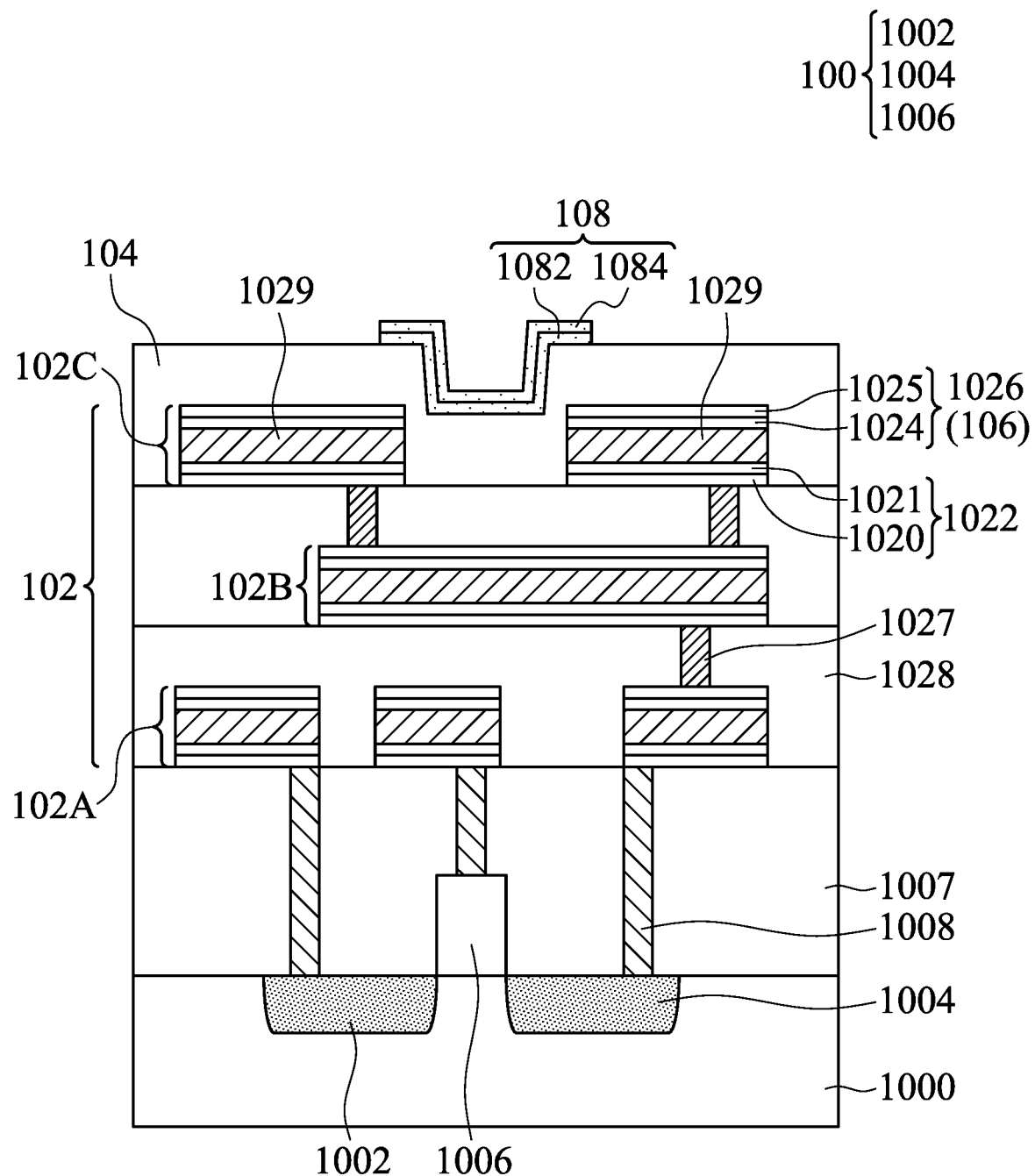

Next, referring to FIG. 4, a passivation layer 104 is formed conformally on the topmost inter-metal dielectric layer 1028 in the interconnect structure 102. The material of the passivation layer 104 may include silicon oxide, silicon nitride, silicon oxynitride, phosphosilicate glass, borophosphosilicate glass, a low-k dielectric material, other suitable dielectric materials, or a combination thereof. The low-k dielectric material may include fluorinated silicate glass, carbon doped silicon oxide, amorphous fluorinated carbon, parylene, benzocyclobutenes, polyimide, or a combination thereof. In one specific embodiment, the material of the passivation layer 104 may be silicon oxynitride.

In some embodiments, the thickness of the passivation layer 104 may range from about 5000 Å to about 7000 Å, such as about 6000 Å. In some embodiments, the refractive index of the passivation layer 104 may range from about 1.6 to about 2.6, such as about 2.0. In some embodiments, the dielectric constant of the passivation layer 104 may range from about 5 to about 10, such as about 7.5. The passivation layer 104 having a refractive index and dielectric constant within the above range may result in better attachment of biomolecules in the bio-sample to the passivation layer 104, thereby increasing the detection accuracy of the capacitive biosensor 10.

Still referring to FIG. 4, a second sensing electrode 108 is formed on the passivation layer 104. The material of the second sensing electrode 108 may be deposited conformally, and then a portion of the material of the second sensing electrode 108 is removed using suitable etching processes to form the second sensing electrode 108. In some embodiments, as shown in FIG. 4, the second sensing electrode 108 has a U-shape profile in the cross-sectional view. In some embodiments, the second sensing electrode 108 may include a first electrode layer 1082 and a second electrode layer 1084 disposed on the first electrode layer 1082. The material of the first electrode layer 1082 may include titanium, tantalum, ruthenium, and the like, or a combination thereof. In one specific embodiment, the material of the first electrode layer 1082 may be titanium. The material of the second electrode layer 1084 may include titanium nitride, titanium oxide, tantalum nitride, tantalum oxide, ruthenium nitride, ruthenium oxide, and the like, or a combination thereof. In one specific embodiment, the material of the second electrode layer 1084 may be titanium nitride. The first electrode layer 1082 and the second electrode layer 1084 may be deposited using suitable deposition techniques, such as physical vapor deposition, atomic layer deposition, metal-organic chemical vapor deposition, other suitable deposition processes, or a combination thereof. In some embodiments, the thickness of the first electrode layer 1082 may range from about 100 Å to about 300 Å, such as about 200 Å. In some embodiments, the thickness of the second electrode layer 1084 may range from about 1000 Å to about 2000 Å, such as about 1500 Å. The second electrode layer 1084 having a thickness within the above range may provide sufficient protection for the underlying first electrode layer 1082 during the analysis of bio-samples, leading to higher stability of the device.

Figure 5A:
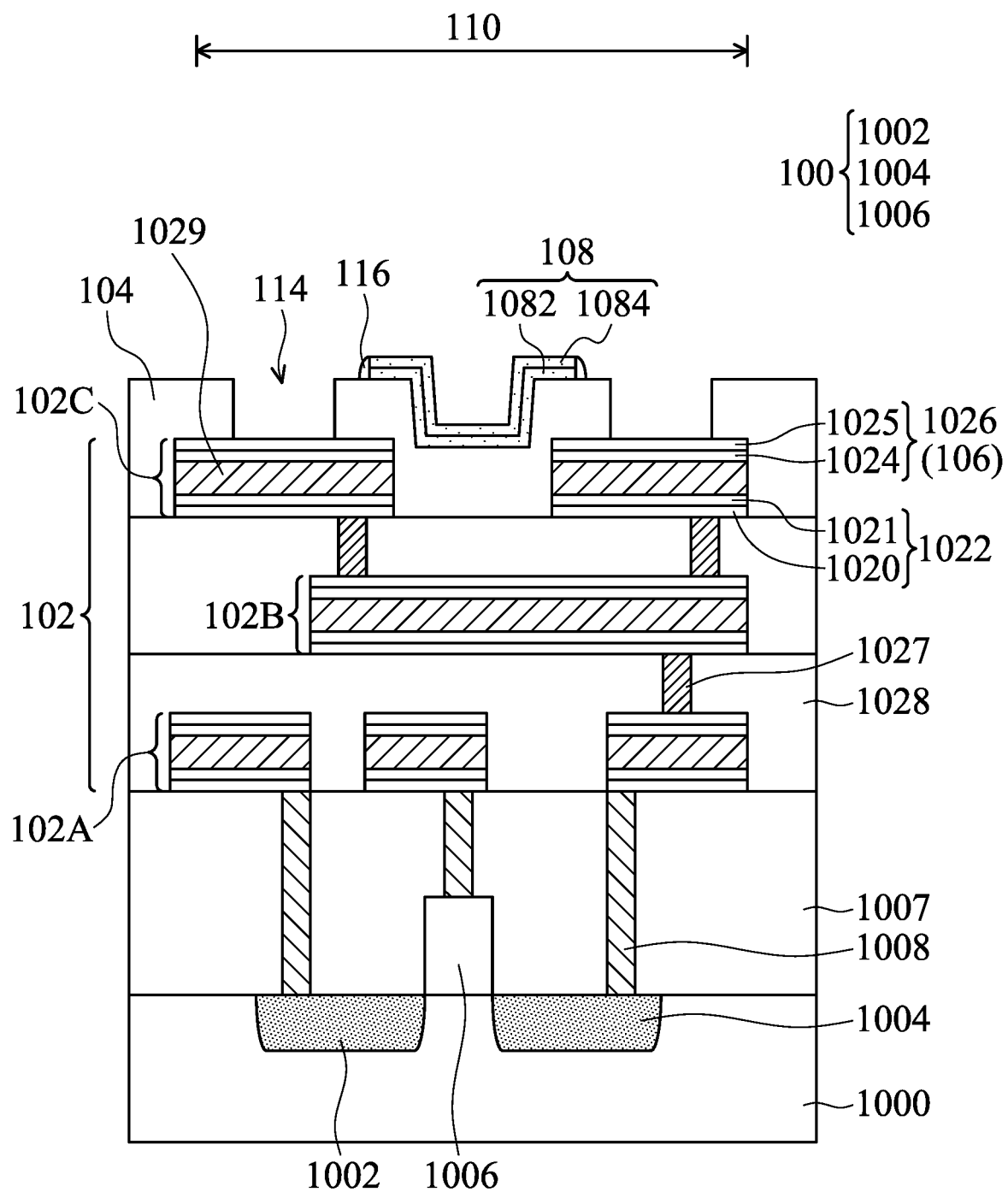

Next, referring to FIG. 5A, a sidewall spacer 116 is formed on sidewalls of the second sensing electrode 108. In some embodiments, the sidewall spacer 116 may be formed of nitride, such as silicon nitride, silicon oxynitride, silicon carbide, silicon carbonitride, and the like, or a combination thereof. In one specific embodiment, the material of the sidewall spacer 116 may be silicon oxynitride. In some embodiments, the refractive index of the sidewall spacer 116 may range from about 1.6 to about 2.6, such as about 2.0. In some embodiments, the dielectric constant of the sidewall spacer 116 may range from about 5 to about 10, such as about 7.5. The sidewall spacer 116 having a refractive index and dielectric constant within the above range may result in better attachment of biomolecules in the bio-sample to a sensing region 110, especially in the vicinity of the second sensing electrode 108, thereby increasing the detection accuracy of the capacitive biosensor 10.

The material of the sidewall spacer 116 may be deposited on the passivation first using suitable deposition processes, such as chemical vapor deposition, physical vapor deposition, atomic layer deposition, other suitable deposition techniques, or a combination thereof. Subsequently, a portion of the material of the sidewall spacer 116 is removed using an anisotropic etching process to form the sidewall spacer 116 on the sidewalls of the second sensing electrode 108. The sidewall spacer 116 may protect the bottom of the second sensing electrode 108 from erosion by acid components of the bio-samples, thereby preventing the performance of the capacitive biosensor 10 from being affected.

Still referring to FIG. 5A, the passivation layer 104 is etched to form an opening 114 exposing the first sensing electrode 106 (i.e., the third conductive layer 1026 on the topmost metal layer 1029). The exposed first sensing electrode 106 may contact bio-samples, and may form a sensing capacitor with the second sensing electrode 108. The region where the exposed first sensing electrode 106 and the second sensing electrode 108 locate is herein referred to as "the sensing region 110". The sensing region 110 is configured to receive an object. The capacitive biosensor 10 of the embodiments of the disclosure may detect the capacitance difference between different bio-samples by the sensing capacitor formed of the first sensing electrode 106 and the second sensing electrode 108, and the composition of the bio-samples may be determined accordingly.

As shown in FIG. 5A, the capacitive biosensor 10 of the embodiments of the disclosure includes the transistor 100, the interconnect structure 102 disposed on the transistor 100, and the passivation layer 104 disposed on the interconnect structure 102. The interconnect structure 102 includes the first metal structure 102A, the second metal structure 102B on the first metal structure 102A, and the third metal structure 102C on the second metal structure 102B. The third metal structure 102C includes the first conductive layer 1022, the second conductive layer 1029 (i.e., the topmost metal layer 1029), and the third conductive layer 1026 that are sequentially stacked. The passivation layer 104 has the opening 114 exposing a portion of the third metal structure 102C. The capacitive biosensor 10 further includes the sensing region 110 disposed on the interconnect structure 102. The sensing region 110 includes the first sensing electrode 106 and the second sensing electrode 108. The first sensing electrode 106 is formed of the third conductive layer 1026 of the third metal structure 102C, and the second sensing electrode 108 is disposed on the passivation layer 104. The capacitive biosensor 10 further includes the sidewall spacer 116 disposed on the sidewalls of the second sensing electrode 108. In some embodiments, the second sensing electrode 108 includes the first electrode layer 1082 and the second electrode layer 1084 disposed on the first electrode layer 1082.

In the embodiments shown in FIGS. 1-4 and 5A, the process for forming the capacitive biosensor may be compatible with the conventional MOS BEOL process. The conductive coating of the topmost metal structure in the interconnect structure may be used as a first sensing electrode of the capacitive biosensor without additional deposition of a layer for the first sensing electrode, thereby resulting in uniform topography of the entire device. Compared to the process without the conventional MOS BEOL process, such as the process in which platinum is used for the electrode material of the biosensor, the complexity and cost of the process for the capacitive biosensor may be reduced by using the conductive coating of the topmost metal structure as the first sensing electrode of the capacitive biosensor. The thickness of the entire device may be reduced, and better structural stability may be achieved. In addition, by using the sidewall spacer to protect the second sensing electrode of the capacitive biosensor, the second sensing electrode may not be eroded by acid components in the bio-samples, and the performance of the capacitive biosensor may be affected accordingly. Moreover, the passivation layer and the sidewall spacer of the capacitive biosensor include the materials with specific properties (e.g., the thickness, the refractive index, and the dielectric constant within the specific range) so that biomolecules in the bio-samples may easily attach to the sensing region formed of the first sensing electrode and the second sensing electrode. As a result, the detection accuracy is increased.

Figure 5B:
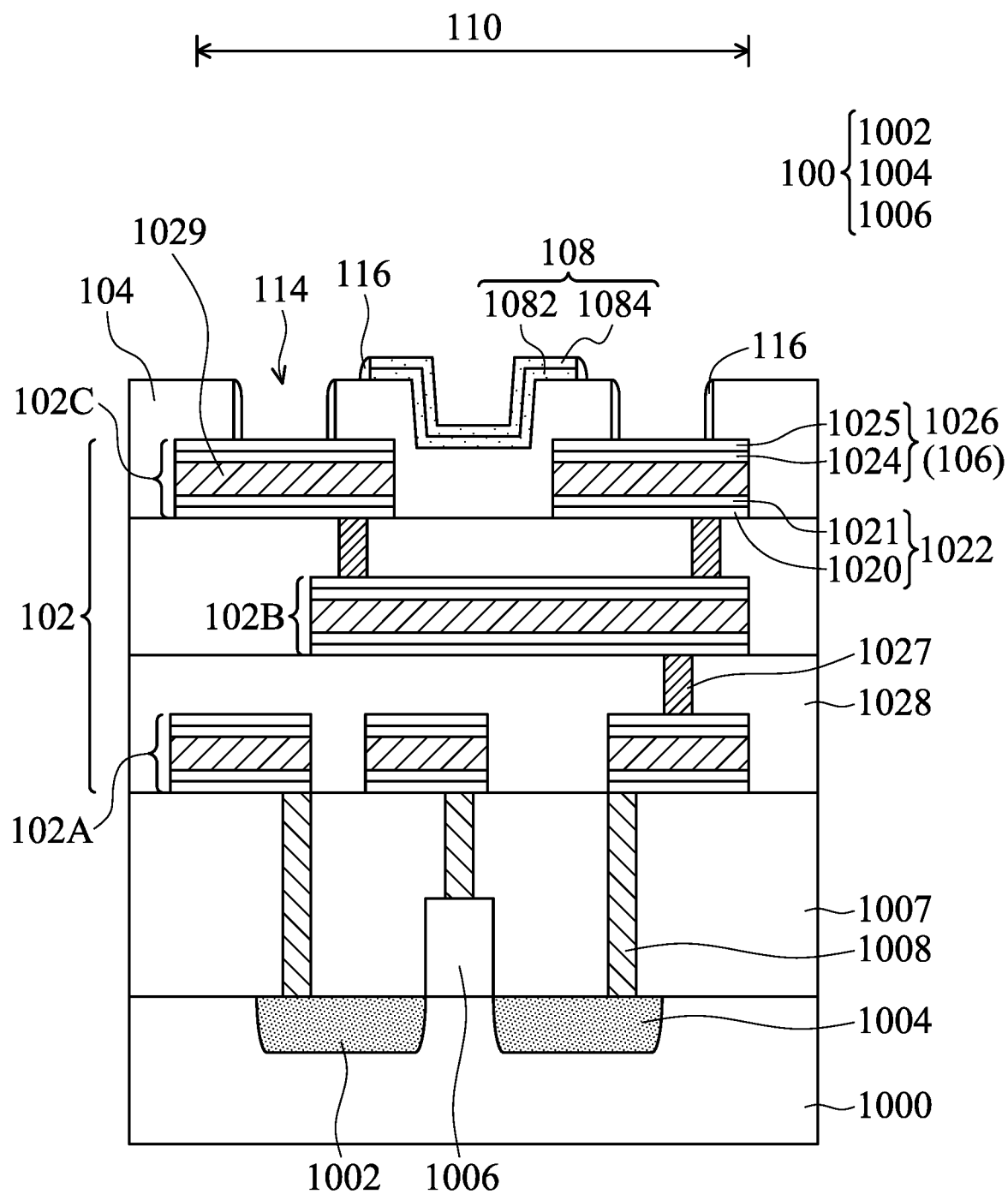
FIG. 5B is a cross-sectional diagram of a capacitive biosensor in accordance with other embodiments of the disclosure.

FIG. 5B is a cross-sectional diagram of the capacitive biosensor 10 in accordance with other embodiments of the disclosure. The difference between the embodiments shown in FIG. 5B and the embodiments shown in FIGS. 1-4 and 5A is that the opening 114 is formed in the passivation layer 104 first, and then the sidewall spacer 116 is formed. Therefore, the sidewalls spacer 116 is formed on the sidewalls of the second sensing electrode 108 as well as on sidewalls of the opening 114. In other words, the sidewall spacer 116 may be formed simultaneously on the sidewalls of the second sensing electrode 108 and the sidewalls of the opening 114 in the same process. As such, the sidewall spacer 116 may not only protect the second sensing electrode 108 in the sensing region 110 but also protect the first sensing electrode 106 from erosion of acid components in the bio-samples.

Figure 6:
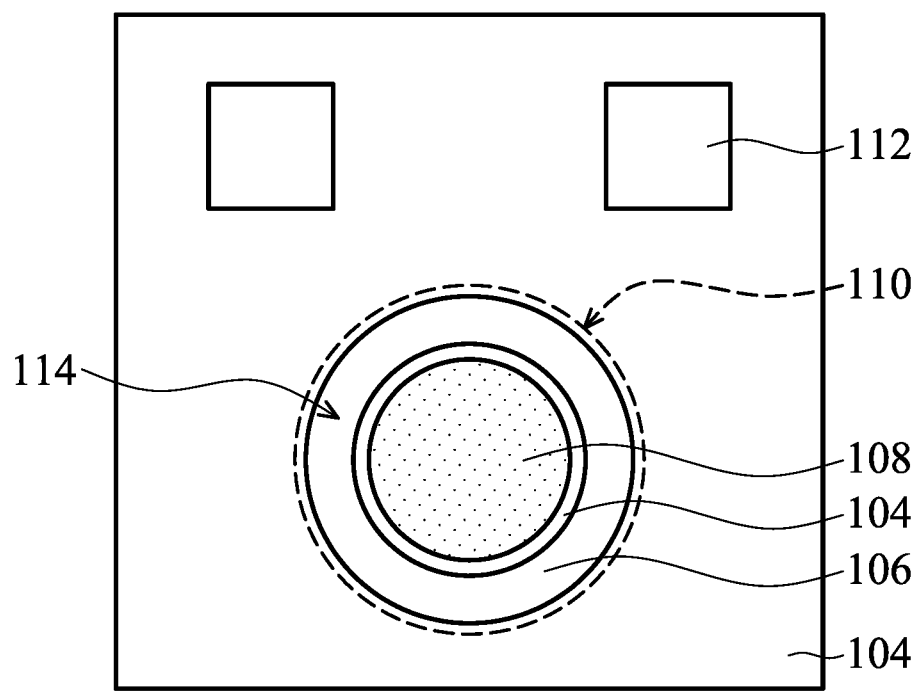
FIG. 6 is a top-view diagram of a capacitive biosensor in accordance with some embodiments of the disclosure.

FIG. 6 is a top-view diagram of the capacitive biosensor 10 in accordance with some embodiments of the disclosure. The sensing region 110 includes the exposed first sensing electrode 106 and the second sensing electrode 108. In some embodiments, as shown in FIG. 6, the opening 114 has a ring structure from the top-view. In the embodiments where the opening 114 has the ring structure from the top-view, the second sensing electrode 108 is disposed in the center of the ring structure of the opening 114. In some embodiments, the capacitive biosensor 10 further includes attachment pads 112. As shown in FIG. 6, the opening 114 may be also formed in the passivation layer 104 outside the sensing region 110 so that the third conductive layer 102६ of the third metal structure 102C outside the sensing region 110 is exposed to be used as the attachment pads 112. The attachments pads 112 are configured to form an electrical connection to exterior devices or to provide exterior signals for the first sensing electrode 106. Although only two attachment pads 112 are shown in FIG. 6, the invention is not limited thereto. In other embodiments, the capacitive biosensor 10 may include more or fewer attachment pads 112.

Figure 7:
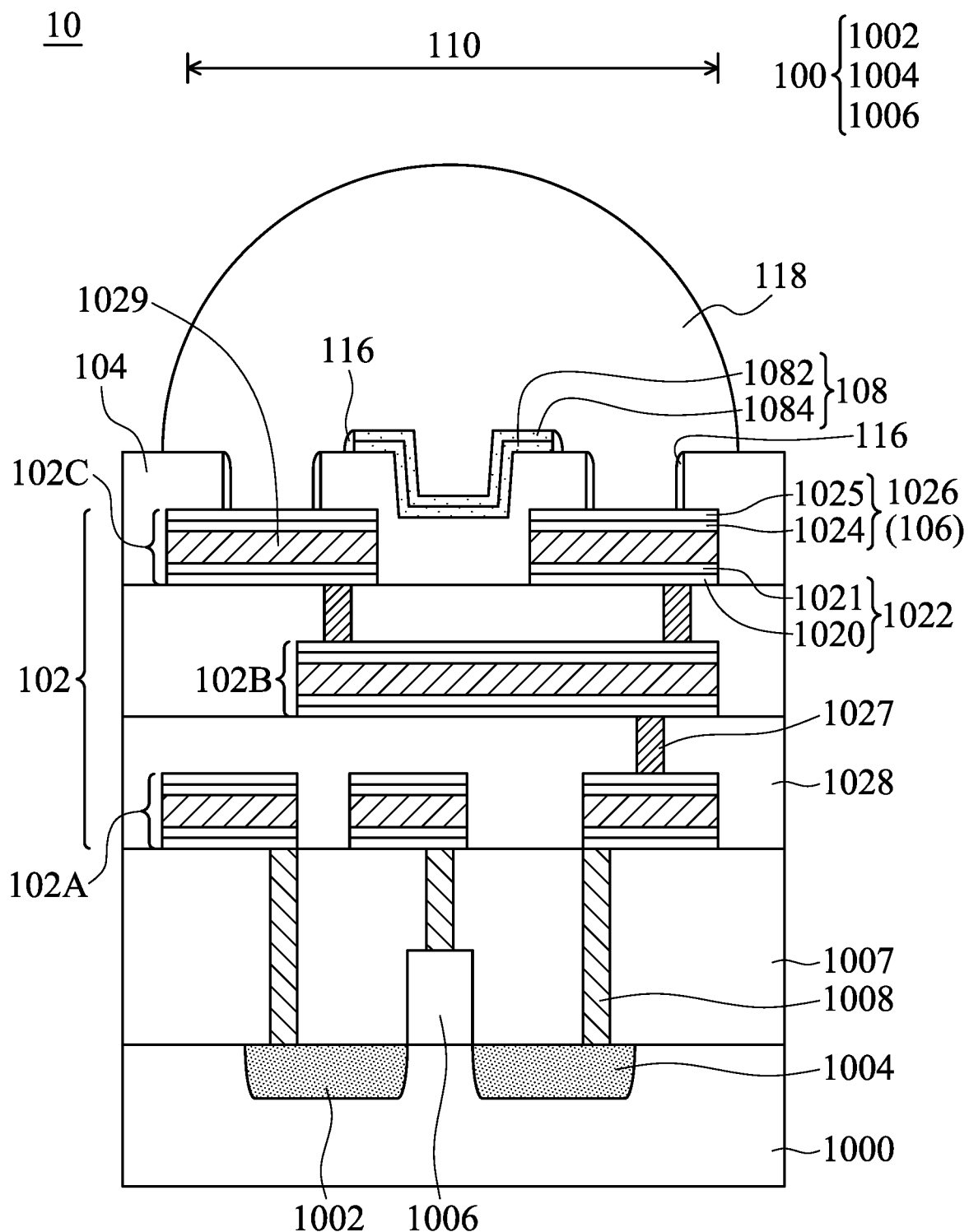
FIG. 7 is an operative diagram of bio-sample detection using the capacitive biosensor of the embodiments of the disclosure.

FIG. 7 is an operative diagram of bio-sample detection using the capacitive biosensor 10 of the embodiments of the disclosure. As shown in FIG. 7, a bio-sample 118 is placed in the sensing region 110 of the capacitive biosensor 10. In some embodiments, the bio-sample 118 may include deoxyribonucleic acid (DNA) or ribonucleic acid (RNA). The droplet formed of the bio-sample 118 may cover the second sensing electrode 108 and the first sensing electrode 106 in the sensing region 110 in which the first sensing electrode 106 is exposed through the opening 114. The capacitive biosensor 10 may make use of the sensing capacitor formed of the first sensing electrode 106 and the second sensing electrode 108 to detect the capacitance difference between different bio-samples 118, thereby determining the composition of the bio-samples 118. Specifically, for example, in the embodiments where the bio-samples 118 include deoxynucleic acid, the capacitive biosensor 10 may make use of the sensing capacitor formed of the first sensing electrode 106 and the second sensing electrode 108 to detect the capacitance difference between different bio-samples 118, thereby determining the base composition (e.g., adenine (A), guanine (G), cytosine (C), and thymine (T)) of deoxynucleic acid in the bio-samples 118.

According to some embodiments of the disclosure, since the passivation layer 104 and the sidewall spacer 116 have the specific refractive index and dielectric constant, deoxynucleic acid in the bio-sample 118 may be easily attach to the sensing region 110. As such, the detection accuracy of the capacitive biosensor 10 may be increased.

In summary, the conventional COMS BEOL process is used for the capacitive biosensor provide by the embodiments of the disclosure. The conductive coating of the topmost metal structure in the interconnect structure is used as the first sensing electrode of the capacitive biosensor without additional deposition of a layer for the first sensing electrode, thereby resulting in uniform topography of the entire device. Compared to the existing biosensor that uses platinum for the electrode material of the biosensor, the complexity and cost of the process may be reduced, the thickness of the entire device may be reduced, and better structural stability may be achieved. In addition, by using the sidewall spacer to protect the first sensing electrode and the second sensing electrode of the capacitive biosensor, the first sensing electrode and the second sensing electrode may not be eroded by acid components in the bio-samples, and the performance of the capacitive biosensor may be not affected accordingly. Moreover, the passivation layer and the sidewall spacer of the capacitive biosensor include the materials with specific properties (e.g., the thickness, the refractive index, and the dielectric constant within the specific range) so that biomolecules in the bio-samples may easily attach to the sensing region formed of the first sensing electrode and the second sensing electrode. As a result, the detection accuracy is increased.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A capacitive biosensor, comprising:
   a transistor;
   an interconnect structure disposed on the transistor, wherein the interconnect structure comprises:
   a first metal structure disposed on the transistor;
   a second metal structure disposed on the first metal structure; and
   a third metal structure disposed on the second metal structure, wherein the third metal structure comprises a first conductive layer, a second conductive layer, and a third conductive layer that are sequentially stacked, and wherein each of the first conductive layer and the third conductive layer comprises a first conductive coating and a second conductive coating on the first conductive coating;
   a passivation layer disposed on the interconnect structure, wherein the passivation layer has an opening exposing a portion of the third metal structure;
   a first sidewall spacer disposed on sidewalls of the opening; and
   a sensing region disposed on the interconnect structure, wherein the sensing region comprises:
   a first sensing electrode formed of the third conductive layer; and
   a second sensing electrode disposed on the passivation layer.

2. The capacitive biosensor as claimed in claim 1, wherein the opening has a ring structure from a top-view, and the second sensing electrode is disposed in the ring structure.

3. The capacitive biosensor as claimed in claim 1, further comprising:
   a dielectric layer disposed between the transistor and the first metal structure;
   a first inter-metal dielectric layer disposed between the first metal structure and the second metal structure; and
   a second inter-metal dielectric layer disposed between the second metal structure and the third metal structure, wherein the third metal structure is electrically connected to the second metal structure through at least two conductive pillars.

4. The capacitive biosensor as claimed in claim 1, wherein the second sensing electrode has a U-shape profile in a cross-sectional view.

5. The capacitive biosensor as claimed in claim 1, further comprising a second sidewall spacer disposed on sidewalls of the second sensing electrode.

6. The capacitive biosensor as claimed in claim 5, wherein the second sidewall spacer comprises a nitride material.

7. The capacitive biosensor as claimed in claim 1, wherein a refractive index of the passivation layer ranges from 1.6 to 2.6.

8. The capacitive biosensor as claimed in claim 1, wherein a dielectric constant of the passivation layer ranges from 5 to 10.

9. The capacitive biosensor as claimed in claim 1, wherein the passivation layer comprises silicon oxide, silicon nitride, silicon oxynitride, phosphosilicate glass (PSG), borophosphosilicate glass (BPSG), fluorinated silicate glass (FSG), carbon-doped silicon oxide, amorphous fluorinated carbon, parylene, benzocyclobutenes (BCB), polyimide (PI), or a combination thereof.

10. The capacitive biosensor as claimed in claim 1, wherein the first conductive coating comprises titanium, tantalum, ruthenium, or a combination thereof, and the second conductive coating comprises titanium nitride, titanium oxide, tantalum nitride, tantalum oxide, ruthenium nitride, ruthenium oxide, or a combination thereof.

11. The capacitive biosensor as claimed in claim 1, wherein a thickness of the first conductive coating ranges from 100 Å to 300 Å, and a thickness of the second conductive coating ranges from 1000 Å to 2000 Å.

12. The capacitive biosensor as claimed in claim 1, wherein the second sensing electrode comprises a first electrode layer and a second electrode layer disposed on the first electrode layer, and wherein the first electrode layer comprises titanium, tantalum, ruthenium, or a combination thereof, and the second electrode layer comprises titanium nitride, titanium oxide, tantalum nitride, tantalum oxide, ruthenium nitride, ruthenium oxide, or a combination thereof.

13. The capacitive biosensor as claimed in claim 12, wherein a thickness of the first electrode layer ranges from 100 Å to 300 Å, and a thickness of the second electrode layer ranges from 1000 Å to 2000 Å.

14. The capacitive biosensor as claimed in claim 1, further comprising a bio-sample covering the first sensing electrode and the second sensing electrode.

15. A method for fabricating a capacitive biosensor, comprising:
providing a transistor;
forming an interconnect structure on the transistor, wherein the interconnect structure comprises:
a first metal structure disposed on the transistor;
a second metal structure disposed on the first metal structure; and
a third metal structure disposed on the second metal structure, wherein the third metal structure comprises a first conductive layer, a second conductive layer, and a third conductive layer that are sequentially stacked, and wherein the third conductive layer forms a first sensing electrode of a sensing capacitor;
depositing a passivation layer on the interconnect structure;
depositing a second sensing electrode of the sensing capacitor on a portion of the passivation layer;
forming an opening in the passivation layer exposing a portion of the third metal structure; and
forming a first sidewall spacer on sidewalls of the opening.

16. The method as claimed in claim 15, further comprising forming a second sidewall spacer on sidewalls of the second sensing electrode before the step of forming the opening in the passivation layer.

17. The method as claimed in claim 15, further comprising forming a third sidewall spacer on sidewalls of the second sensing electrode after the step of forming the opening in the passivation layer, wherein the third sidewall spacer and the first sidewall spacer are formed in the same step.

18. The method as claimed in claim 15, wherein a dielectric constant of the passivation layer ranges from 5 to 10.

19. The method as claimed in claim 15, wherein the first conductive coating comprises titanium, tantalum, ruthenium, or a combination thereof, and the second conductive coating comprises titanium nitride, titanium oxide, tantalum nitride, tantalum oxide, ruthenium nitride, ruthenium oxide, or a combination thereof.

20. The method as claimed in claim 15, wherein the second sensing electrode comprises a first electrode layer and a second electrode layer disposed on the first electrode layer, and wherein the first electrode layer comprises titanium, tantalum, ruthenium, or a combination thereof, and the second electrode layer comprises titanium nitride, titanium oxide, tantalum nitride, tantalum oxide, ruthenium nitride, ruthenium oxide, or a combination thereof.

\* \* \* \* \*